United States Patent [19]

Bush

[11] Patent Number: 5,439,954

[45] Date of Patent: Aug. 8, 1995

[54] SUBSTITUTED PHENYL-1,3-DIKETONES AS PROTECTANTS AGAINST SKIN DAMAGE

[75] Inventor: Rodney D. Bush, Fairfield, Ohio

[73] Assignee: The Procter & Gamble Company, Cincinnati, Ohio

[21] Appl. No.: 776,506

[22] Filed: Oct. 11, 1991

[51] Int. Cl.⁶ .......................... A61K 7/06; A61K 7/42; A61K 9/10; C11D 3/48
[52] U.S. Cl. ...................... 424/59; 252/106; 252/107; 424/DIG. 5; 424/47; 424/60; 424/70.9; 514/844; 514/847; 514/938; 514/944; 556/1
[58] Field of Search .......................................... 424/59

[56] References Cited

U.S. PATENT DOCUMENTS

| | | | |
|---|---|---|---|
| 3,082,071 | 3/1963 | Hartle et al. | 44/68 |
| 3,937,737 | 2/1976 | Eiglmeier | 424/59 |
| 3,994,869 | 11/1976 | Gontarz et al. | 526/1 |
| 4,015,980 | 4/1977 | MacKay et al. | 75/120 |
| 4,065,502 | 12/1977 | MacKay et al. | 423/34 |
| 4,082,807 | 4/1978 | Eiglmeier | 560/144 |
| 4,123,400 | 10/1978 | Gay | 260/23 |
| 4,152,396 | 5/1979 | MacKay et al. | 423/139 |
| 4,175,012 | 11/1979 | MacKay | 204/108 |
| 4,387,089 | 6/1983 | DePolo | 424/59 |
| 4,489,057 | 12/1984 | Welters et al. | 424/47 |
| 4,710,373 | 12/1987 | Nakamura et al. | 424/59 |
| 4,988,501 | 1/1991 | Gosciniak | 424/59 |
| 5,191,121 | 3/1993 | Yamada et al. | 564/305 |

FOREIGN PATENT DOCUMENTS

| | | | |
|---|---|---|---|
| 856814 | 10/1977 | Belgium . | |
| 0313305 | 4/1989 | European Pat. Off. | A61K 7/40 |
| 0431755 | 6/1991 | European Pat. Off. | A61K 7/42 |
| 02/227484-A | 9/1990 | Japan | C09K 3/00 |
| 91-16034 | 10/1991 | WIPO | A61K 7/42 |
| 91-16035 | 10/1991 | WIPO | A61K 7/42 |

OTHER PUBLICATIONS

Chem. Abstracts, vol. 78 (11): 71176h, Shapet'ko, 1976.
Chem. Abstracts, vol. 94: 30776r, Ishikawa, 1981.
Chem. Abstracts, vol. 96: 148054y, Smirnova et al., 1982.
Bissett, D. L., R. Chatterjee & D. P. Hannon, "Chronic Ultraviolet Radiation-Induced Increase in Skin Iron and the Photoprotective Effect of Topically Applied Iron Chelators", Photochemistry and Photobiology, vol. 54, No. 2 (1991), pp. 215-223.
Chemical Abstracts CA89(13):108947r. (1979).

Primary Examiner—Dale R. Ore
Attorney, Agent, or Firm—John M. Howell; Milton B. Graff, IV; Jerry J. Yetter

[57] ABSTRACT

The subject invention relates to pharmaceutical compositions comprising a safe and effective amount of a compound having the structure:

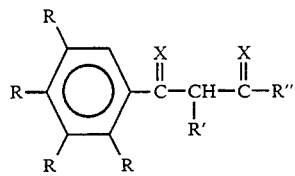

wherein each R is alkyl or hydrogen, at least two being alkyl; R' is hydrogen, alkyl or aryl; R" is alkyl or halo; and each X is independently oxygen or sulfur; and a pharmaceutically-acceptable carrier. The subject invention also relates to methods for preventing damage to skin by topically applying a safe and effective amount of such compounds to the skin.

17 Claims, No Drawings

SUBSTITUTED PHENYL-1,3-DIKETONES AS PROTECTANTS AGAINST SKIN DAMAGE

TECHNICAL FIELD

The subject invention relates to topical pharmaceutical compositions useful for protecting the skin from the harmful effects of radiation, particularly ultraviolet radiation, such as sunburn and sun-induced premature aging of the skin. The subject invention involves compounds exhibiting activity both as absorbers of ultraviolet (UV) light and as metal chelators which inhibit production of free radicals.

BACKGROUND OF THE INVENTION

The damaging effects of radiation, particularly sunlight, on skin are well documented. Much damage is due to routine day-to-day activities in the sunlight.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, American Pharmaceutical Association, Washington, D.C., 1982, pp. 499–511; Grove and Forbes, "A Method for Evaluating the Photoprotection Action of Sunscreen Agents Against UV-A Radiation", *International Journal of Cosmetic Science*, vol. 4 (1982), pp. 15–24; and U.S. Pat. No. 4,387,089 issued to DePolo on Jun. 7, 1983. Although the immediate effects of ultraviolet radiation may be cosmetically and socially gratifying, the long-term hazards are cumulative and potentially serious.

Sunblock agents are commercially available to protect the skin from UV radiation. These agents scatter or reflect ultraviolet radiation. Examples include titanium dioxide and zinc oxide. However, these agents are very susceptible to rub-off or wear-off, resulting in little or no protection.

The most common agents for sun protection are sunscreens. These agents exert their effects through absorption of ultraviolet radiation so that it cannot penetrate the skin. Sunscreens must remain on the surface of the skin during exposure to be effective. However, sunscreens are easily rubbed off or washed off by sweating or swimming and can also be lost by penetration into the skin.

Tocopherol (Vitamin E) and its esters have been disclosed for use as photoprotectors in topical compositions, without interfering with the tanning response; see, e.g., U.S. Pat. Nos. 4,144,325 issued to Voyt on Mar. 13, 1974; 4,248,861 issued to Schutt on Feb. 3, 1981; 4,000,276 issued to Hasunuma et al., on Dec. 28, 1976; 4,847,071 issued to Bissett, Bush & Chatterjee on Jul. 11, 1989; and European Patent Application No. 166,221 of Tuominen published Jan. 2, 1986.

Hart, J. R., "Chelating Agents in Cosmetic and Toiletry Products", *Cosmetics and Toiletries*, Vol. 93, No. 12 (1978), pp. 28–30, discloses the utilization of low levels of chelating agents such as ethylenediaminetetraacetic acid (EDTA) in cosmetic formulations as preservatives. Particularly disclosed is the use of EDTA in sunscreen lotions and creams to prevent dark color formation from the reaction of p-aminobenzoic acid derivatives with iron; see also, Hart, J. R., "EDTA-Type Chelating Agents in Personal Care Products", *Cosmetics and Toiletries*, Vol. 98, No. 4 (1983), pp. 54–58. Japanese Patent Application 61-215,314 discloses a topical composition for protecting skin from UV-rays containing EDTA or a phosphoric acid or salt, 4-(1,1-dimethylethyl)-4′-methoxydibenzoylmethane and inorganic powders. The acids and their salts are added as preservatives; see also, Japanese Patent Application 61-215,313, published Sep. 25, 1986; and U.S. Pat. No. 4,579,844 issued to Rovee on Apr. 1, 1986. Wooley, D. E., R. W. Glanville, D. R. Roberts & J. M. Evanson, "Purification, Characterization and Inhibition of Human Skin Collagenase", *Biochem. J.*, Vol. 169 (1978), pp. 265–276, discloses the inhibition of skin collagenase utilizing EDTA, 1,10-phenanthroline, cysteine, dithiothreitol, or sodium aurothiemaleate.

It is well-known that various types of radiation, particularly ultraviolet light radiation, induce inflammation of the skin and harmful photochemical reactions therein. During exposure, and as repair of the radiation damage takes place, super-oxide ($O_2^-$) radicals are formed in the skin. UV irradiation also causes some microvascular damage in the skin; see Kligman, L. H. & A. M. Kligman, "The Nature of Photoaging: Its Prevention and Repair", *Photodermatology*, Vol. 3 (1986), pp. 215–227. This leads to local hemorrhage and "leakage" of blood cells into the dermis. Iron from the hemoglobin accumulates in the extra-cellular matrix of the tissue as $Fe^{+2}$ and $Fe^{+3}$. It is known that iron catalytically participates in the conversion of superoxide radicals to hydroxyl radicals, a species which is known to be very damaging to tissue; see Davies, K. J. A., M. E. Delsignore & S. W. Lin, "Protein Damage and Degradation by Oxygen Radicals. II. Modification of Amino Acids", *The Journal of Bioloqical Chemistry*, Vol. 262, No. 20 (1987), pp. 9902–9907. Another process which is damaging to tissue is membrane lipid peroxidation, which is also accelerated by iron; see Halliwell and Gutteridge, *Free Radicals in Biology and Medicine*, Claredon Press, Oxford, England (1985), p. 147.

Black, H. S., "Potential Involvement of Free Radical Reactions in Ultraviolet Light-Mediated Cutaneous Damage", *Photochemistry and Photobiology*, Vol. 46, No. 2 (1987), pp. 213–221, speculates, based on circumstantial evidence, that free radicals may cause at least some UV-induced skin damage. The effect of systemically or intraperitoneally administered antioxidants on peroxide formation is discussed.

Nunez, M. T., E. S. Cole & J. Glass, "The Reticulocyte Plasma Membrane Pathway of Iron Uptake as Determined by the Mechanism of $\alpha,\alpha'$-Dipyridyl Inhibition", *The Journal of Biological Chemistry*, Vol. 258, No. 2 (1983), pp. 1146–1151, discusses the cellular mechanism by which iron is released by reticulocytes. It was found that iron (II) chelators (e.g., phenanthroline, dipyridyl), but not iron (III) chelators, were useful in the study of this mechanism.

deMello Filho, A. C. & R. Meneghini, "Protection of Mammalian Cells by o-Phenanthroline from Lethal and DNA-Damaging Effects Produced by Active Oxygen Species", *Biochemica et Biophysica Acta,* Vol. 847 (1985), pp. 82–89, describes cell culture work which suggests that the inhibition of the iron-initiated peroxidation reaction by phenanthroline may prevent cellular damage caused by inflammation.

Morgan, E. H. "Chelator-Mediated Iron Efflux from Reticulocytes". *Biochemica et Biophysica Acta,* Vol. 733, No. 1, (1983), pp. 39–50, discusses the mechanism by which certain iron chelators inhibit cellular iron uptake after release from transferrin while it is still in the membrane fraction of the cells.

Bissett, D. L., R. Chatterjee & D. P. Hannon, "Chronic Ultraviolet Radiation-Induced Increase in Skin Iron and the Photoprotective Effect of Topically Appl led Iron Chelators", *Photochemistry and Photobiology,* Vol. 54, No. 2 (1991), pp. 215–223, discloses that iron may have a role in skin photo-damage by participating in formation of reactive oxygen species, such as hydroxyl radical, and that certain iron chelators delay the onset of skin photodamage.

European Patent Application No. 0 313 305 of Bissett, Bush & Chatterjee published April 26, 1989, discloses photoprotection compositions comprising various chelating agents.

References which disclose certain substituted phenyl-1,3-diketones and various uses for such compounds include the following: U.S. Pat. Nos. 3,937,737 and 4,082,807 issued to Eiglmeier on Feb. 10, 1976 and Apr. 4, 1978, respectively; U.S. Pat. No. 3,994,869 issued to Gontarz & Nelson on Nov. 30, 1976; U.S. Pat. No. 4,015,980 issued to MacKay & Sudderth on Apr. 5, 1977; U.S. Pat. No. 4,123,400 issued to Gay on Oct. 31, 1978; U.S. Pat. No. 4,152,396 issued to MacKay & McDonald on May 1, 1979; U.S. Pat. No. 4,175,012 issued to McKay & Rogier on Nov. 20, 1979; and Belgian Patent No. 856,814 of Hoechst AG, published Oct. 31, 1977.

Substituted phenyl-1,3-diketone compounds disclosed to have ultraviolet light absorbing properties are disclosed in the following references: U.S. Pat. Nos. 4,387,089 issued to DePolo on Jun. 7, 1983; U.S. Pat. No. 4,489,057 issued to Welters, Gehlhaus & Moeschl on Dec. 18, 1984; U.S. Pat. No. 4,710,373 issued to Nakamura, Hattori, Tamura, Tajima, Takaishi, Imokawa & Hotta on Dec. 1, 1987; U.S. Pat. No. 4,988,501 issued to Gosciniak on Jan. 29, 1991; and Japanese Patent Publication No. 02,227,484-A of Hasegawa KK, published Sep. 10, 1990; and European Patent Application No. 0,431,755 of Unilever PLC, published Jun. 12, 1991.

It is an object of the subject invention to provide topical pharmaceutical compositions which provide protection against damage to the skin from sun exposure and other radiation sources.

It is also an object of the subject invention to provide methods for preventing damage to the skin due to exposure of skin to the sun and other radiation sources.

It is a further object of the subject invention to provide methods for preventing damage to the skin due to metal-catalyzed free radical generation in the cells of the skin.

SUMMARY OF THE INVENTION

The subject invention relates to pharmaceutical compositions comprising a safe and effective amount of a compound having the structure:

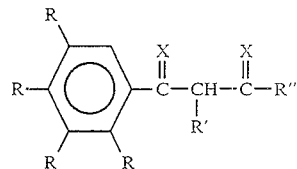

wherein each R is independently alkyl or hydrogen, at least two being alkyl; R' is hydrogen, alkyl or aryl; R" is alkyl or halo; and each X is independently oxygen or sulfur; and a pharmaceutically-acceptable carrier. The subject invention also relates to methods for preventing damage to skin by topically applying a safe and effective amount of such compounds to the skin.

DETAILED DESCRIPTION OF THE INVENTION

As used herein, "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indictated, alkyl are preferably as follows. Preferred akyl are straight or branched chain, more preferably straight chain. Preferred alkyl are mono-, di-, or tri-, or unsubstituted, more preferably monosubstituted or unsubstituted, most preferably unsubstituted. Preferred alkyl are saturated or monounsaturated, more preferably saturated. As used herein, "alkanyl" means a saturated alkyl group; "alkenyl" means an alkyl having one or more double bonds in the carbon chain; "alkynyl" means an alkyl having one or more triple bonds in the carbon chain. Preferred alkyl are $C_1$–$C_{20}$, more preferably $C_1$–$C_{16}$, more preferably still $C_1$–$C_{12}$, still more preferably $C_1$–$C_8$, more preferably still $C_1$–$C_6$, still more preferably $C_1$–$C_4$, more preferably still $C_1$–$C_2$, most preferably $C_1$.

As used herein, "aryl" means an aryl ring which may be substituted or unsubstituted. Except where otherwise indicated, aryls are preferably mono-, di-, or trisubstituted or unsubstituted, more preferably monosubstituted or unsubstituted, most preferably unsubstituted. Preferred aryls are phenyl and naphthyl, especially phenyl.

As used herein, "substituted", in reference to alkyl or aryl groups, means such groups that can be mono- or polysubstituted. Preferred substituents are selected from the group consisting of halogen, hydroxy, amino, nitro, carboxy, thio, aryl, alkyl, alkoxy, and aryloxy.

As used herein, "safe and photoprotectively effective amount" means an amount sufficient to substantially reduce the deleterious effects of ultraviolet radiation to skin but not so much as to cause serious side effects or adverse skin reactions.

As used herein, "regulating" means preventing, retarding, or arresting.

As used herein, all percentages are by weight unless otherwise specified.

The subject invention involves compounds, referred to herein as "active compounds", having the structure:

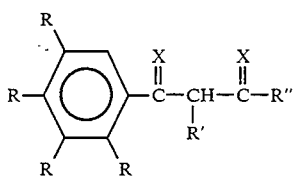
(1)

wherein each R is independently alkyl or hydrogen, at least two being alkyl; R' is hydrogen, alkyl or aryl; R" is alkyl or halo; and each X is independently oxygen or sulfur.

Preferred R are alkanyl. Preferred R are unsubstituted or substituted with alkyl, alkoxy, hydroxy or halogens; more preferred R are unsubstituted. Preferred R are straight chain. Preferred R are $C_1$–$C_4$; more preferred R are methyl and ethyl; most prefered R is methyl.

Preferred compounds include 2,3-, 2,4-, 2,5-, 3,4- and 3,5-dialkylphenyl-; 2,3,4-, 2,3,5-, 2,4,5-, and 3,4,5-trialkylphenyl-; and 2,3,4,5-tetraalkylphenyl-1,3-diketone compounds. It is also preferred that all non-hydrogen R's be the same.

If R' is aryl, it is preferably unsubstituted or substituted phenyl, preferably unsubstituted. If substituted, preferred aryl substituents are $C_1$–$C_4$ alkyl, more preferably methyl or ethyl, especially methyl; hydroxy, $C_1$–$C_4$ alkoxy, especially ethoxy or particularly methoxy, or halo, especially fluoro or chloro.

If R' is alkyl, it is preferably unsubstituted. If substituted, preferred alkyl substituents include halo, especially fluoro or chloro; hydroxy; and phenyl.

Most preferred is R' being hydrogen.

R" is preferably straight or branched chain, substituted or unsubstituted $C_1$–$C_8$, more preferably $C_1$–$C_4$, more preferably still $C_1$–$C_2$, most preferably $C_1$, alkyl. R" is preferably unsubstituted; if substituted, preferred substituents include hydroxy and halo, especially fluoro and chloro. R' is preferably saturated.

Preferred X is oxygen.

The active compounds useful in the subject invention are generally moderate UV-light absorbers, but provide surprisingly high values in an SPF test (based on Test Method III hereinbelow). The active compounds are also good metal chelators and provide protection against chronic skin aging and wrinkling due to metal catalyzed free radical formation, which may be caused by skin exposure to UV-light or other causes. Therefore, the compositions of the subject invention which comprise the active compounds can provide excellent protection against both short term (acute) and long term (chronic) exposure to UV-light and against damage due to other causes of metal-catalyzed free radical formation.

Active compounds useful in the subject invention also include metal complexes of the compounds of structure (1). The active compounds of structure (1) are metal chelators and readily form complexes with metal ions. The inclusion of metal complexed active compounds in the compositions of the subject invention can enhance the acute photoprotection provided by the composition, but may reduce the chronic photoprotection, since it may tie up a substantial portion of the chelating ability of the active compound. A metal ion generally complexes with from about 1 to about 4 molecules of an active compound of structure (1).

Preferred metal ions for inclusion in the metal complexed active compounds useful in the subject invention include sodium, aluminum, zinc, iron, lithium, magnesium, potassium, calcium, rubidium, strontium, titanium, zirconium, vanadium, chromium, manganese, cobalt, nickel, copper, gallium, scandium, silicon, boron, praseodymium, lanthanum, promethium, samarium, and europium; more preferred metal ions are those which do not have d-electrons: sodium, aluminum, zinc, lithium, magnesium, potassium, calcium and scandium; most preferred metal ions are sodium, aluminum, zinc, lithium, gallium and scandium.

Preferred active compounds useful in the subject invention include the following:
1-(2',5'-dimethylphenyl)-1,3-butanedione
1-(2',4'-dimethylphenyl)-1,3-butanedione
1-(3',4'-dimethylphenyl)-1,3-butanedione
1-(2°,3',4'-trimethylphenyl)-1,3-butanedione
1-(2',3',5'-trimethylphenyl)-1,3-butanedione
1-(2',4',5'-trimethylphenyl)-1,3-butanedione
1-(3',4',5'-trimethylphenyl)-1,3-butanedione
1-(2',3',4',5'-tetramethylphenyl)-1,3-butanedione The following examples exemplify the synthesis of active compounds useful in the subject invention.

EXAMPLE 1

1-(2',3',4',5'-tetramethylphenyl)-1,3-butanedione: 1369.4 g of 1,2,3,4-tetramethylbenzene (Willey Chemical Co., 99+% pure) and 2931.5 mL of acetic anhydride are placed in a 12 L flask under positive nitrogen and chilled to 3° C. in an ice-bath. 8.63 L of borontrifluoride acetic acid is added while maintaining the temperature below 5° C. The reaction is stirred via mechanical stirrer for two hours. The reaction is warmed to room temperature and stirred for two hours. The reaction mixture is heated to 65° C. for 20 hours followed by cooling to room temperature. The reaction mixture is poured into a solution containing 17 L of water and 6442.7 g of sodium acetate trihydrate. (It is important to add the reaction solution to the sodium acetate.) This mixture is heated to reflux for 30 minutes, followed by cooling to room temperature. This mixture is extracted with 4 gallons of methylene chloride. The resulting water layer is extracted with two gallons of methylene chloride. The combined methylene chloride layers are dried over 6 lbs. of sodium sulfate. The mixture is filtered and evaporated to give 1630 g of liquid; distillation at 115°–124° C. and 0.01 mm Hg results in 1017 g of 1-(2',3',4',5'-tetramethylphenyl)-1,3-butanedione.

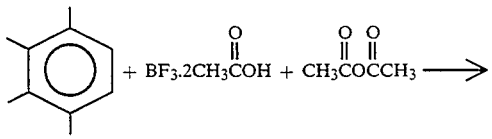

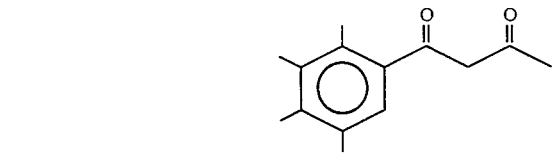

Analytical Methods

TLC: Analtech GHLF silica gel TLC plates are eluted with 1% acetic acid/1,2-dichloroethane. The resulting r.f. values are 0.706 for 1-(2',3',4',5'-tetramethylphenyl)-1,3-butanedione and 0.616 for the intermediate 1-(2',3',4',5'-tetramethylphenyl)ethane-2-one, an undesired impurity.

GC: Hewlett-Packard instrument (Model 5890A) using a 30 m×0.25 mm ID DB-5, film thickness 0.25 microns glass capillary column (J&W Scientific, cat. #122-5032) with injection at 150° C. for 3 minutes then 10° C. per minute to 250° C. for 2 minutes. The sample injected is 1 mg/mL in toluene. The resulting retention times are 7.7 minutes for 1-(2',3',4',5'-tetramethylphenyl)ethane-2-one, an undesired impurity, and 11.6 minutes for 1-(2',3',4',5'-tetramethylphenyl)-1,3-butanedione.

EXAMPLE 2

1-(2',3',4'-trimethylphenyl)-1,3-butanedione: 50 g of 1,2,3-trimethylbenzene (Aldrich Chemical Co., 90+% pure) and 160 mL of acetic anhydride are placed in a 1 L flask under positive nitrogen and chilled at 3° C. in an ice-bath. 462 mL of boron trifluoride acetic acid is added while maintaining the temperature below 5° C. The reaction mixture is stirred via mechanical stirrer for two hours. The reaction mixture is warmed to room temperature and stirred for two hours. The reaction mixture is heated to 65° C. for 20 hours followed by cooling to room temperature. The reaction mixture is poured into a solution containing 900 mL of water and 208 g of sodium acetate anhydrous. (It is important to add the reaction solution to the sodium acetate.) This mixture is heated to reflux for 30 minutes, followed by cooling to room temperature. This mixture is extracted with 800 mL of methylene chloride. The resulting water layer is extracted with 200 mL of methylene chloride. The combined methylene chloride layers are dried over 146 g of sodium sulfate. The dark brown organic fraction is acidic pH and smells strongly of acetic acid. The liquid is transferred to a 4 L separatory funnel. Saturated sodium bicarbonate (aq) is added 100 mL at a time (a total of 2100 mL is added) to neutralize the sample. Addition of the sodium bicarbonate is done slowly because the sample foams and much gas evolves in the neutralization process. The mixture is filtered through a cake of sodium sulfate (anhydrous) and is evaporated to give 150 g of a very dark brown viscous liquid. This material is distilled, 150° C. and 0.01 mm Hg, to yield 24.3 g of 1-(2',3',4'-trimethylphenyl)-1,3-butanedione. This material is distilled again, at 0.01 mm Hg using a mirrored column and a receiver cow to collect fractions. A total of four fractions are collected with a total weight of 15.53 g. All fractions are green in color. Results of this distillation are:

b. pt. 94°–101° C. 0.3 g of pale green liquid
b. pt. 101°–106° C. 1.8 g of pale green liquid
b. pt. 107° C. 3.3 g of green liquid
b. pt. 107°–115° C. 9.8 g of green liquid In an attempt to remove the color, a 2 g sample of the fourth fraction is worked-up in the following manner. The 2 g sample is treated with 0.95 eq (9.3 mL) of 1N NaOH, aq. The sample is extracted with 10 mL of CH$_2$Cl$_2$. The aqueous layer is treated with 0.95 eq (9.3 mL) of 1N HCl, aqueous. The resulting solution is milky. This solution is extracted 2× with 10 mL each of CH$_2$Cl$_2$. The organic fraction is run through anhydrous MgSO$_4$. Evaporation results in 1.1 g of product which is a pale yellow viscous oil.

Analytical Methods

TLC: Analtech GHLF silica gel-TLC plates are eluted with 1% acetic acid/1,2-dichloroethane. The resulting r.f. values are 0.79 for 1-(2',3',4'-trimethylphenyl)-1,3-butanedione and 0.85 for the intermediate 1-(2',3',4'-trimethylphenyl)ethane-2-one, an undesired impurity.

GC: Hewlett-Packard instrument (Model 8590A) using a 30 m×0.25 mm ID DB-5, film thickness 0.25 microns glass capillary column (J&W Scientific, cat. #122-5032) with injection at 150° C. for 3 minutes then 10° C. per minute to 250° C. for 2 minutes. The sample injected is 1 mg/mL in toluene. The resulting retention time is 10.8 minutes for 1-(2',3',4'-trimethylphenyl)-1,3-butanedione.

Other compounds of interest having different R substituents on the phenyl ring can be synthesized by methods similar to Examples 1 and 2 by substituting the 1,2,3,4-tetramethylbenzene or 1,2,3-trimethylbenzene, respectively, with the desired substituted benzene. Other compounds of interest having different R″ moieties can be synthesized by methods similar to Examples 1 and 2 by substituting the acetic acid and acetic anhydride with an acid and anhydride having the desired moiety. Boron tri-fluoride-organic acid complex is made by bubbling BF$_3$ through the respective acid.

Compositions of the subject invention comprise a safe and effective amount of an active compound useful in the subject invention disclosed hereinabove, preferably from about 0.1% to about 25%, more preferably from about 0.5% to about 10%, more preferably still from about 1% to about 5%.

In addition to the active compound, the compositions of the subject invention comprise a topical pharmaceutically-acceptable carrier. The term "pharmaceutically-acceptable carrier", as used herein, means one or more compatible solid or liquid filler diluents or encapsulating substances which are suitable for administration to a human or lower animal. Such carriers must be of sufficiently high purity and sufficiently low toxicity to render them suitable for administration to the human or lower animal being treated. Such carrier preferably comprises from about 75% to about 99.9%, more preferably from about 90% to about 99.5%, more preferably still from about 95% to about 99% of the composition.

Topical Carriers

The topical compositions of the subject invention may be made into a wide variety of product types. These include, for example, lotions, creams, beach oils, gels, sticks, sprays, ointments, pastes, mousses and cosmetics. These product types may comprise either of two basic types of carrier systems, solutions and emulsions.

The topical compositions of the subject invention formulated as solutions typically include a pharmaceutically-acceptable aqueous or organic solvent. Preferred solvents, in addition to being capable of having dispersed or dissolved therein the active compound, also possesses acceptable safety (e.g., irritation and sensitization characteristics), as well as good aesthetic properties (e.g., does not feel greasy or tacky). Water is a typical aqueous solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanediol, and mixtures thereof. Preferred solutions of the subject invention contain from about 0.01% to about 20%, more preferably from about 0.5% to about 10%, more preferably from about 1% to about 5% of the active compound, and from about 80% to about 99.99%, more preferably from about 90% to about 99.5%, more preferably from about 95% to about 99% of an acceptable organic solvent.

If the topical compositions of the subject invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972).

Topical compositions of the subject invention may be formulated as a solution comprising an emollient. An example of a composition formulated in this way would be a beach oil product. Such compositions typically comprise from about 0.01% to about 20%, preferably from about 0.1% to about 10%, more preferably from about 0.5% to about 5% of the active compound and from about 1% to about 50%, preferably from about 5% to about 20% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 0.1% to about 20%, preferably from about 0.5% to about 10%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the subject invention would comprise from about 0.1% to about 20%, preferably from about 0.5% to about 10%, of the active compound; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segatin, Cosmetics, Science and Technology, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickeft et al.,; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference.

Preferred emulsifiers are anionic or nonionic, although the other types may also be used.

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the subject invention. In general, such single or multiphase emulsions contain water, emollients and emulsifiers as essential ingredients.

Triple emulsion carrier systems comprising an oil-in-water-in-silicone fluid emulsion composition as disclosed in U.S. patent application Ser. No. 022,876, Figueroa, et al., filed Mar. 6, 1987, herein incorporated by reference, are also useful in the subject invention. This triple emulsion carrier system can be combined with from about 0.1% to about 20%, preferably from about 0.5% to about 10%, of the active compound to yield the topical pharmaceutical/cosmetic composition of the subject invention.

Another emulsion carrier system useful in the topical compositions of the subject invention is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 0.5% to about 10% of the active compound.

Lotions and creams can be formulated as emulsions as well as solutions. Typically such lotions comprise from about 0.1% to about 20%, preferably from about 0.5% to about 10%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.1% to about 20%, preferably from about 0.5% to about 10%, of the active compound; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the topical compositions of the subject invention are formulated as a gel or a cosmetic stick, a suitable amount of a thickening agent, as disclosed supra, is added to a cream or lotion formulation.

The topical compositions of the subject invention may also be formulated as makeup products such as foundations, or lipsticks.

The topical compositions of the subject invention may contain, in addition to the aforementioned components, a wide variety of additional oil-soluble materials and/or water-soluble materials conventionally used in topical compositions, at their art-established levels.

Various water-soluble materials may also be subject in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical compositions of the subject invention may also include a safe and effective amount of a penetration enhancing agent. A safe and effective amount is generally from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published Jan. 13, 1982.

Other conventional skin care product additives may also be included in the compositions of the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the subject invention. For example, Vitamin A, and derivatives thereof, Vitamin $B_2$, biotin, pantothenic, Vitamin D, and mixtures thereof may be used.

Compositions of the subject invention can be tested using the following test methods to determine effective dosage levels of the active compound and appropriate formulations and methods of application. For example, if an active compound from Test Method 1 is not effective in a given formulation in Test Method 2, it may be due to inability of the agent to penetrate the skin from the formulation. A formulation with a skin penetration enhancer may be needed in order to achieve the desired result.

Test Method I

Standard Method for Assay of Ornithine Decarboxylase Activity

Scope: This method describes an assay procedure for the determination of the enzyme ornithine decarboxylase (ODC) in mouse skin epidermis. The assay is linear up to at least 40 minutes of incubation of enzyme with substrate, with a deviation between replicates of less than 10%. The method is based on published procedures for determination of mouse epidermal ODC. (See Lowe, N., A. K. Verma, and R. K. Boutwell, *Journal of Investigational Dermatology,* Vol. 71 (1978), pp. 417–418; Verma, A. K., N. J. Lowe & R. K. Boutwell, *Cancer Research,* Vol. 39 (1979), pp. 1035–1040; Binder, R. L., M. E. Volpenheim & A. A. Motz, *Carcinogenesis,* Vol. 10 (1989), pp. 2351–2357; and Hillebrand, G. G., M. S. Winslow, M. J. Benzinger, D. A. Heitmeyer & D. L. Bissett, "Acute and Chronic Ultraviolet Radiation Induction of Epidermal Ornithine Decarboxylase Activity in Hairless Mice", *Cancer Research,* Vol. 50 (1990), pp. 1580–1584.)

Principle: A homogenate of mouse epidermal tissue is incubated with carbon 14-labeled L-ornithine, the substrate for the enzyme. The enzyme catalyzes the release from ornithine of $^{14}CO_2$, which is trapped with benzethonium hydroxide. The $^{14}C$ is then counted versus substrate to determine amount of liberated $CO_2$. The amount of liberated $CO_2$ is used to determine the level of enzyme present in the tissue. There are no available standards for this mouse skin enzyme. Previous work (see Hillebrand) has indicated the conditions under which this assay can be done to obtain a linear correspondence between time of enzyme-substrate incubation and release of $^{14}CO_2$.

Chemicals:

1. $NaH_2PO_4.H_2O$
2. $Na_2HPO_4.7H_2O$
3. EDTA (ethylene diamine tetracetic acid), disodium, dihydrate
4. PLP (pyridoxal phosphate)
5. DTT (dithiothreitol)
6. L-ornithine. HCl
7. L-[1-$^{14}C$]-ornithine.HCl (52 mCi/mmole; Dupont NEN Products, Boston, Mass.)
8. Anhydrous citric acid
9. Methylbenzethonium hydroxide (1M solution in methanol; Sigma Chemical Co., St. Louis, Mo.)
10. Bio-Rad Protein Assay Kit—based on Bradford protein assay (See Randford, M., *Anal. Biochemistry,* Vol. 72 (1976), p. 248.)

See note at end of method.

Equipment:

1. Clear polystyrene tubes (12×75 mm, #14-956-3D, Fisher Scientific, Pittsburgh, Pa.)
2. Tissue homogenizer—Tissuemizer (type SDT-1810, Tekmar, Co., Cincinnati, Ohio)
3. 1.5 ml polypropylene micro test tubes (#223-9500, Bio-Rad Laboratories, Richmond, Calif.)
4. Eppendorf centrifuge (model 5415; Brinkman Instruments Inc., Westbury, N.Y.)
5. Pasteur pipettes.
6. Cryogenic vials (#07753-0308), Vangard Cryos, Vangard International Inc., Neptune, N.J.)
7. 15×85 mm and 16×150 mm glass test tubes
8. 37° C. shaking water (Aquatherm water bath shaker model R-86, New Brunswick Scientific Co., New Brunswick, N.J.)
9. Kontes Scientific (Vineland, N.J.) rubber stoppers (#882310-0000) and center well assemblies (#882320-0000)
10. Magnetic stirrer and Teflon-coated magnetic stir bars
11. Glass beakers (100, 250 and 500 ml sizes, and 1 and 2 liter sizes).
12. 50 ml polypropylene centrifuge tubes (#25331, Corning Glass Works, Corning, N.Y.)
13. Vortex mixer
14. Spectrophotometer (model 260, Gilford Instrument Laboratories, Inc., Oberlin, Ohio)
15. Whatman No. 1 filter paper
16. Polypropylene funnel See note at end of method.

Preparation of Special Reagents:

1. Homogenization buffer: Homogenization buffer=50 mM sodium phosphate, 1.25 mM EDTA, 2.5 mM DTT and 0.1 mM PLP [pH 7.1].
   (a) Dissolve 3.45 g of $NaH_2PO_4.7H_2O$ and 0.23 g EDTA in 400 ml of distilled-deionized water; bring volume to 500 ml: 50 mM monobasic sodium phosphate+1.25 mM EDTA.
   (b) Dissolve 6.7 g of $Na_2HPO_4.H_2O$ and 0.23 g of EDTA in 400 ml of distilled-deionized water; bring volume to 500 ml: 50 mM dibasic sodium phosphate+1.25 mM EDTA.

Combine 250 ml of (a) with 500 ml of (b) to yield 750 ml of pH 7.1 phosphate-EDTA buffer. Add 0.289 g of DTT to 750 ml of phosphate-EDTA buffer and then 0.0185 g of PLP to 750 ml of phosphate-EDTA-DTT buffer to prepare final homogenization buffer. This is prepared in advance and kept frozen at −20° C. in 50 ml aliquats in 50 ml polypropylene centrifuge tubes until needed. Then it is thawed, and kept on ice.

2. Substrate solution: Substrate solution=1.6 mM L-ornithine, 0.65 mM PLP, 20 micro Ci/ml L-[$^{14}$C]-ornithine. Dissolve 34 mg of L-ornithine in 100 ml of water. To this is added 20 mg of PLP. This is frozen in 1-ml aliquats until used. Mix 1 ml of the ornithine-PLP mixture with 0.25 ml (25 micro Ci) of L-[1-$^{14}$C]-ornithine hydrochloride (52 mCi/mmole; Dupont NEN Products, Boston, Mass.). This substrate solution is de-gassed (to remove any $^{14}CO_2$) by pulling a partial vacuum (aspirator) on the solution three times, each of 30 seconds duration. This solution is then kept at room temperature until used.
3. Citric acid solution: Dissolve 384 g of citric acid in 600 ml of water; bring the volume up to 1000 ml: 2M citric acid (pH 1.5). This is prepared in advance and kept frozen at −20° C. in 50-ml aliquats in 50 ml polypropylene centrifuge tubes until needed. Then it is thawed, and kept at room temperature.
4. Dye Reagent: Dilute 1 volume of Dye Reagent Concentrate with 4 volumes of distilled-deionized water. Filter through Whatman No. 1 filter paper and store dilute reagent in a glass container at room temperature. Prepare just before use.
5. Protein standard: The Bio-Rad Protein Standard supplied in the kit is lyophilized bovine protein sealed under nitrogen. To reconstitute, add 20 ml of distilled-deionized water which will yield a protein concentration of 1.4 mg/ml. This protein solution is stored at −20° C. until needed. Then it is thawed, and kept at room temperature.

Mouse Treatment and Irradiation. A compound to be tested is dissolved in a liquid vehicle; preferred vehicles are ethanol, isopropanol, water, propylene glycol, or mixtures thereof. The test material solution is 5% (w/v) test compound (or saturated with test compound if the test compound is not soluble at 5% in any reasonable vehicle).

Test material solutions are applied topically to the dorsal skin of the mouse. A control group of mice receives topical application of the same vehicle as is in the test material solution (without the active compound). Test material solution or control vehicle is applied to the skin of each mouse at an application rate of approximately 2 $\mu$l/cm$^2$. Topical treatments are done three times: AM and PM of Day 1 and AM of Day 2.

Two hours after the third treatment, the dorsal skin of the mice is exposed to 2×MED (minimum erythemal dose) with a 1000-watt Xenon arc solar simulator. The total UV dose is approximately 1.6 J/cm$^2$. Twenty-four hours after irradiation, mice are sacrificed by cervical dislocation, and the dorsal skin is removed.

Procedure:
1. Whole dorsal skin from a mouse is placed dermis side down on an ice cold glass plate. The epidermal side of the skin is scraped with a razor blade 20 times to remove the epidermis, which adheres to the razor blade.
2. Epidermal shave scrapings are transferred to individual 12×75 mm clear polystyrene tubes containing 0.6 ml of ice cold homogenization buffer.
3. Using a Tissuemizer homogenizer, the tissue is homogenized on ice for 20 seconds at a homogenizer power control setting of 80 (0–100 scale).
4. The homogenate is transferred to a 1.5 ml polypropylene micro test tube and centrifuged at 16,000× g for 10 minutes at 4° C. in an Eppendorf centrifuge.
5. The clear supernatant solution is transferred with a Pasteur pipette to a 1.2 cc cryogenic vial.
6. Add 0.1 ml of supernatant solution to a 15×85 mm glass test tube and place in a 37° C. shaking water bath for 5 minutes. Duplicate assays are run for each sample. Six blank assays containing 0.1 ml of homogenization buffer are also run.
7. The assay is started by addition of 0.025 ml of de-gassed substrate solution. This gives a final concentration of assay components of 40 mM sodium phosphate, 1 mM EDTA, 2 mM DTT, 0.2 mM PLP, 0.4 mM ornithine, and 0.5 micro Ci of $^{14}$C-ornithine. The assay tube is immediately sealed with a rubber stopper and center well assembly, the center well containing 0.1 ml of methylbenzethonium hydroxide. The reaction is run at 37° C. in a shaker water bath at 50 rpm for 30 minutes.
8. Using a disposable 1 ml plastic syringe fitted with a 22 gauge 1.5-inch needle, the assay is stopped by piercing the rubber stopper and injecting 0.25 ml of 2M citric acid solution into the assay solution. Particular care is taken not to inject citric acid into the center well assembly.
9. The assay mixture is kept at room temperature for 30 minutes after citric acid injection to ensure complete absorption of $^{14}CO_2$ by methylbenzethonium hydroxide contained in the center well.
10. The center well bucket is transferred, by cutting with scissors the center well stem, to scintillation vials containing 10 ml of scintillation fluid and shaken thoroughly. Standards are prepared by adding 0.025 ml of substrate solution to 10 ml of scintillation fluid; this amount of $^{14}$C represents total conversion of substrate to $CO_2$ in the assay.
11. Content of $^{14}$C is determined with a scintillation counter.
12. Determine protein content of homogenate by the Bio-Rad Protein Assay. Place 0.02 ml of homogenate and 0.08 ml of water in a test tube (16×150 mm). As blanks, 0.02 ml of homogenization buffer is used. All assays are done in duplicate. Add 5 ml of diluted dye reagent. Mix on a vortex mixer. After 5 minutes to 1 hour, measure OD$_{595}$ versus blanks. Protein content of samples is read from a plot of OD$_{595}$ versus concentration of protein standards (20–140 microgram).

Calculations: Based on the total dpm in the L-[$^{14}$C]-ornithine standard, the dpm per pmole of $^{14}$C can be derived. The following equations are then used to calculate ODC activity on the basis of protein:

$$\frac{\text{dpm sample} - \text{dpm blank}}{\text{dpm/pmole }^{14}C \times 0.1 \text{ ml} \times 0.5 \text{ hour} \times \text{mg protein/ml}} = \frac{\text{pmole}}{\text{hr mg}}$$

The Ornithine Decarboxylase (ODC) value (pmole/hr mg) for the test compound is compared to the ODC value (pmole/hr mg) for the control to give a percent difference between the two values. Preferred active compounds useful in the subject invention demonstrate at least a 20% decrease, preferably at least a 50% decrease, in the ODC value as compared to the ODC value of the control.

NOTE: The chemicals and equipment specified in these sections are described in detail as to properties, dimensions, and suggested suppliers for the convenience of those doing the assay. Unless otherwise indicated, alternate sources of equivalent chemicals and equipment may be used, providing that they meet the requirements necessary to preserve the accuracy and precision of the assay method.

Test Method II

In Vivo Mouse Skin Wrinkling Test

A second test useful for screening compounds for photoprotective capability is the in vivo mouse skin wrinkling test which measures premature wrinkling inhibition, described in D. L. Bissett, D. P. Hannon & T. V. Orr, "An Animal Model of Solar-Aged Skin: Histological, Physical, and Visible Changes in UV-Irradiated Hairless Mouse Skin", *Photochem. Photobiol.*, Vol. 46 (1987), pp. 367–378; and D. L. Bissett, G. G. Hillebrand and D. P. Hannon, "The Hairless Mouse as a Model of Skin Photoaging: Its Use to Evaluate Photoprotective Materials", *Photodermatology*, Vol. 6 (1989), pp. 228–233.

The test is used to determine the photoprotective efficacy of topically applied materials against UVB-induced photo-aging. The work is done with Skh:HR-1 hairless mice.

A test compound is dissolved in a liquid vehicle; preferred vehicles are ethanol, isopropanol, water, propylene glycol, or mixtures thereof. The test material solution is 5% (w/v) test compound (or saturated with test compound if the test compound is not soluble at 5% in any reasonable vehicle).

Test material solutions are applied topically to the dorsal skin of the mouse. A control group of mice receives topical application of the same vehicle as is in the test material solution (without the active compound). Test material solution or control vehicle is applied to the skin of each mouse at an application rate of approximately 2 $\mu l/cm^2$. Topical treatments are done three times each week.

A bank of four 4-foot fluorescent UVB lamps (Westinghouse FS-40 sunlamps) is used. The energy output of the lamps is measured with an International Light (Newburyport, Mass.) model 700 A research radiometer. Mice are irradiated with 30 $mJ/cm^2$ of UVB per exposure. Irradiations are done two hours after each topical application of the test material solution or vehicle.

Once each week, mice are observed for skin wrinkling and tumor formation. (See Bissett, et al., *Photochem. Photobiol.*, Vol. 46 (1987), pp. 367–378 and Bissett, et al., *Photodermatology*, Vol. 6 (1989), pp. 228–233.) Wrinkles are graded on a 0–3 scale, and tumors are counted as described in these references. The test is continued until the skin wrinkle grade of the control group is at least about 2.0 and the tumors are recounted at this point; generally the test requires about 20 weeks to complete.

Compounds which exhibit at least about a 20% reduction in skin wrinkle grade in Test Method II are useful in the subject invention. Preferred active compounds exhibit at least about a 30% reduction in skin wrinkle grade; more preferred active compounds exhibit at least about a 60% reduction in skin wrinkle grade; most preferred active compounds exhibit at least about a 90% reduction in skin wrinkle grade.

A composition of the subject invention may be tested using Test Method II to determine its effective dosage levels and appropriate formulations and methods of application. For example, if a compound shown to be effective using Test Method I is shown in Test Method II to be a relatively ineffective photo-protective agent due to its inablility to penetrate the skin, it may be formulated with a skin penetration enhancer to enhance its efficacy.

Test Method III

Guinea Pig SPF Method

The guinea pig is used as a model for determination of sun protection factor (SPF) values of topical protective agents; see, e.g., Leroy, D. & P. Deschamps, "Sunscreen Seawater Resistance: Comparison of Human and Guinea-pig Test Models", *Photodermatol.*, Vol. 2 (1985), pp. 38–40; and Bissett, D. L., J. F. McBride, D. P. Hannon, & L. F. Patrick, "Time-dependent Decrease in Sunscreen Protection Against Chronic Photodamage in UVB-irradiated Hairless Mouse Skin", *J. Photochem. Photobiol. B: Biol.*, Vol. 9 (1991), pp. 323–334; and "Sunscreen Drug Products for Over-the-counter Human Drugs", *Federal Register* (Food and Drug Administration), Vol. 43 (1978) p. 38259; all of which are incorporated herein by reference. This animal develops an erythemal response to UV radiation which is very similar to the human response, and photoprotective agent SPF values are similar in the two species.

Materials and Methods

Animals—Male Hartley strain guinea pigs are obtained from Charles River Laboratories, Portage, Mich. The guinea pigs weigh approximately 300 g at the start of experimental work. All animals are housed in individual cages in a room with controlled temperature and humidity and with a 12-hour light/darkness cycle. They are given a standard Purina Chow diet and water ad libitum.

UV Radiation Source and Radiometer—A model 81172 Oriel Corp. (Stratford, Conn.) solar simulator equipped with a 1000-watt zenon arc ozone-free lamp is used. Schott Glass Technologies, Inc. (Duryea, Pa.) filters (a 3-mm WG-305 (to remove UVC) and a 1-mm UG-5 filter (to remove visible light)) are inserted in the light path just past the simulator output port to simulate the solar UV spectrum. Total UVB or UVA output is determined with an International Light (Newburyport, Mass.) model IL1350 radiometer equipped with SED 240 (UVB) and SED 015 (UVA) sensors. Spectral scans are recorded on a model 4950 strip chart recorder (Bausch & Lomb, Austin, Tex.) using an International Light double monochrometer spectro-radiometer system (model IL 700A/760/791). Guinea Pig SPF Measurements—The dorsal skin of guinea pigs is shaved with electric clippers and then depilated with Neet ®Lotion Hair Remover (Whitehall Laboratories, New York, N.Y.). The skin is rinsed under warm tap water and dried with a towel. Sixteen hours later, the dorsal skin is treated with 2 $mg/cm^2$ of test material solution.

The animals (n=5 per treatment group) are then wrapped with 3-inch wide tape (Elastoplast ®, Beiersdorf Inc., Norwalk, Conn.) containing four 2-cm diameter exposure windows (two windows on each side of the spinal area). The adhesive side of the tape covering the dorsal skin area is coated with black construction paper to prevent reddening of the skin from adherence of the tape to that skin region. The time between topical treatment and irradiation with UV-light is approximately 15 minutes.

Animal s are restrained with a neck clip and exposed individually. Each animal is positioned with its dorsal skin surface 18 inches below the filter set of the solar simulator. The irradiance at this distance is approxiamtely 0.45 mW/cm$^2$ UVB and 10.2 mW/cm$^2$ UVA. Irradiation times of the four exposure windows on each animal are set to bracket the suspected SPF of the material being tested. Exposure windows are covered with opaque tape at the end of each time point. At the completion of all irradiations, all tape is removed from the animals.

Erythema is scored (0–3 grading scale, with half grade increments) 24 hours later, using non-exposed adjacent skin on each animal as no UV control (score=0). A grade of 1.0 (detectable redness over the entire exposure area) is considered 1 MED. SPF is then calculated from the ratio: (UV dose to achieve 1 MED with test material)/(UV dose to achieve 1 MED without test material ).

The compositions of the subject invention can contain other photoprotectively active compounds such as sunscreens, sunblocks, anti-inflammatories, antioxidants or radical scavengers.

Combination Actives

A. Sunscreens and Sunblocks

Optimum protection against sun damage can be obtained by using a combination of the active compounds of the subject invention together with sunscreens or sunblocks. Useful sunblocks include, for example, zinc oxide and titanium dioxide.

If the photoprotecting capability of the active compound is primarily active against UVB radiation, a combination of the active compound with a UVA sunscreen would be most desirable. Conversely, if the active compound is primarily active against UVA radiation, a combination of the active compound with a UVB sunscreen would be most desirable. Additional UVA and/or UVB protection may also be included in such compositions. The inclusion of sunscreens in compositions of the subject invention at low levels will not significantly reduce the tanning response of the user but will enhance immediate protection against acute UV damage.

A wide variety of conventional sunscreening agents are suitable for use in combination with the active compounds. Segarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl ); Diazoles (2-acetyl -3bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and violuric acids; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; t-Butylmethoxydibenzoylmethane; Etocrylene; and 4-isopropyldibenzoylmethane.

Of these, 2-ethylhexyl p-methoxycinnamate, 4,4't-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-(bis(hydroxypropyl))aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid, 7-diethylamino-4-methylcoumarin and mixtures of these compounds, are particularly useful.

Preferred sunscreens useful in the compositions of the subject invention are 2-ethylhexyl p-methoxycinnamate, butylmethoxydibenzoylmethane, 2-hydroxy-4-methoxybenzophenone, octyldimethyl p-aminobenzoic acid and mixtures thereof.

A safe and photoprotectively effective amount of sunscreen may be used in the compositions of the subject invention. The sunscreening agent must be compatible with the active compound. Generally the composition may comprise from about 1% to about 20%, preferably from about 2% to about 10%, of a sunscreening agent. Exact amounts will vary depending upon the sunscreen chosen and the desired Sun Protection Factor (SPF). Because of the photoprotecting capability of the active compound against erythema, the combination provides an SPF greater than that of the sunscreen alone.

Also particularly useful in the subject invention are sunscreens such as those disclosed in U.S. Pat. No. 4,937,370 issued to Sabatelli on Jun. 26, 1990, and in U.S. Pat. No. 4,999,186 issued to Sabatelli and Spirnak on Mar. 12, 1991, both incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

The compositions of the subject invention, with or without sunscreens, may also be formulated as shampoos, conditioners, mousses or other hair care products. It is known that UV radiation damages hair and the photoprotecting agents of the subject invention may minimize such damage. Furthermore such formulations will provide a means for applying the photoprotecting agents of the subject invention onto the scalp, which is also susceptible to UV damage. Any compatible art-recognized hair care formulations can be used with the active compound added at a level of from about 1% to about 5%. If desired, a sunscreen may also be included at from about 1% to about 5%.

An agent may also be added to any of the compositions of the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred photoprotection composition of the subject invention, an anti-inflammatory agent is included as an active along with the active compound. The inclusion of an anti-inflammatory agent enhances the photoprotection benefits of the compositions. The anti-inflammatory agent protects strongly in the UVA radiation range (though it also provides some UVB protection as well). The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989; and U.S. Pat. No. 4,847,069, Bissett and Chatterjee, issued Jul. 11, 1989, both incorporated herein by reference.) It has also been discovered that the combination of an anti-inflammatory agent and the active compound provides greater photoprotection than is provided by each active alone.

A safe and effective amount of an anti-inflammatory agent may be added to the compositions of the subject invention, generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal antiinflammatory for use in the subject invention is hydrocortisone.

A second class of anti-inflammatory agents which is useful in the compositions of the subject invention includes the non-steroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), both incorporated herein by reference.

Specific non-steroidal anti-inflammatory agents useful in the composition of the subject invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clidanac, oxepinac, and felbinac;
4) the lenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and
6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the subject invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)-3'-methyl-5'-hexynoyl)-2,6-di-t-butyl-phenol; 4-((R)-(+)-3'-methyl-5'-hexynoyl)-2,6-di-t-butyl phenol; and 4-(3',3'-dimethoxypropionyl)-2,6-di-t-butylphenol are useful in the subject invention.

Yet another class of anti-inflammatory agents which are useful in the subject invention are those disclosed in U.S. Pat. No. 4,912,248, Mueller, issued Mar. 27, 1990. This patent discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the subject invention.

Finally, so-called "natural" anti-inflammatory agents are useful in the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

An even more preferred composition of the subject invention comprises an active compound, a sunscreen, and an anti-inflammatory agent together for photoprotection in the amounts disclosed for each individually hereinabove.

The photoprotection compositions of the subject invention may comprise, in addition to the active compound, a safe and photoprotectively effective amount of a radical scavenging compound, generally from about 1% to about 20%, preferably from about 2% to about 10%, more preferably from about 3% to about 5% of the composition. Examples of such radical scavenging compounds are ascorbic acid (Vitamin C) and its salts, tocopherol (Vitamin E), other tocopherol esters, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxyfumaric acid and its salts. Each of these compounds has photoprotecting capabilities. The use of the radical scavenger tocopherol sorbate in the subject invention in combination with the active compound is preferred.

C. Anti-Oxidants/Radical Scavengers.

In a preferred photoprotection composition of the subject invention, an anti-oxidant/radical scavenger is included as an active along with the active compound. The inclusion of an anti-oxidant/radical scavenger increases the photoprotection benefits of the composition.

A safe and photoprotectively effective amount of an antioxidant/radical scavenger may be added to the compositions of the subject invention, generally from about 0.1% to about 10%, preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, amino-guanidine), sulfhydryl compounds (e.g., glutathione), and dihydroxy fumaric acid and its salts may be used.

In a preferred photoprotection composition of the subject invention, compositions comprise one, any two, or all three of a sunscreening agent, anti-inflammatory agent, and/or an antioxidant/radical scavenging agent included as actives along with the active compound. The inclusion of two or all three of these agents with the active compound increases the photoprotection benefits of the composition.

Method For Preventing Deleterious Effects Caused By UV Exposure

The subject invention further relates to a method for protecting the skin of humans and lower animals from the deleterious effects of radiation, particularly UV radiation, and/or other causes of metal-catalyzed free radical production in the skin tissue. Such protection by the active compound extends to damage resulting from acute UV exposure, e.g. erythema. It also extends to protection from damage resulting from chronic UV exposure, e.g. photoaging. Such protection also extends to damage resulting from sources of radiation other than the sun; non-limiting examples include ultraviolet lights (e.g., tanning lights), x-rays, lasers, etc.

Such a method comprises applying to the skin of the human or lower animal a safe and effective amount of the active compounds disclosed hereinabove to be useful in the subject invention. This may be accomplished by using a composition comprising the active compound as disclosed hereinabove. The active compounds involved in each of the following methods may be simply spread over the skin, or rubbed into the skin to enhance penetration of the active compound. The active compounds are preferably applied in conjunction with UV exposure, i.e., prior to, during, or after UV exposure. More specifically, the active compounds are preferably applied from several hours, preferably up to 4 hours, prior to UV exposure, to up to 30 minutes after UV exposure, or anytime in between.

For protection against acute damage from UV radiation, topical application of the active compounds prior to exposure of the skin to UV radiation is preferred.

For protection against chronic damage from UV radiation, topical application of the active compounds is preferably done on a chronic basis. The active compounds are preferably topically applied to the skin about daily, preferably prior to substantial exposure of the skin to UV radiation. Such application preferably occurs from at least about once to about 5 times daily, more preferably about 2 times daily, but for particularly effective compositions preferably once daily. Such application preferably occurs over long periods of time, preferably for more than one month, more preferably for more than six months, more preferably stll i 11 for more than one year, 5 years, 10 years or more.

Typically a safe and photoprotectively effective amount of an active compound is from about 0. 001 mg to about 1.0 mg, preferably from about 0.01 mg to about 0.5 mg, more preferably from about 0.05 mg to about 0.1 mg of the active compound per $cm^2$ skin.

A preferred method of the subject invention for preventing deleterious effects caused by UV exposure involves applying both a safe and photoprotectively effective amount of an active compound and a safe and photoprotectively effective amount of one or more of an additional sunscreening agent, an anti-inflammatory agent, and/or a radical scavenging compound (as defined hereinbefore) to the skin simultaneously. By "simultaneous application" or "simultaneously" is meant applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.01 mg to about 1.0 mg, preferably from about 0.05 mg to about 0.5 mg, per cm² of skin. The amount of radical scavenging compound applied is generally from about 0.01 mg to about 1.0 mg, preferably from about 0.05 mg to about 0.5 mg, per cm² skin. The amount of anti-inflammatory agent is generally from about 0.005 mg to about 0.5 mg, preferably from about 0.01 mg to about 0.1 mg.

The following examples further describe and demonstrate the preferred embodiments within the scope of the subject invention. The examples are given solely for the purpose of illustration, and are not to be construed as limitations of the subject invention since many variations thereof are possible without departing from its spirit and scope.

EXAMPLE 3

A moisturizing lotion is prepared by combining the following components utilizing conventional mixing techniques.

| Components | Percent by Weight of Composition |
| --- | --- |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| $C_{12}$–$C_{15}$ Alcohol Benzoate (Finsolv TN - commercially available from Finetex, Inc.) | 2.00 |
| 1-(2',3',4'-trimethylphenyl)-1,3-butanedione | 2.00 |
| Dimethicone | 0.30 |
| Imidazolidinyl Urea | 0.10 |
| Ethylene Acrylate Copolymer | 3.80 |
| Tyrosine | 0.10 |
| Water | qs |

This lotion may be topically applied to inhibit damage caused by radiation, particularly acute or chronic UV exposure. Use of an amount of lotion sufficient to deposit about 0.5 mg/cm² of 1-(2',3',4'-trimethylphenyl)-1,3-butanedione to the skin is appropriate.

EXAMPLE 4 & 5

Skin lotions are prepared by combining the following components utilizing conventional mixing techniques.

| Component | Percent by Weight of Composition | |
| --- | --- | --- |
| | Example 4 | Example 5 |
| 4-N,N-(2-Ethylhexyl)methylaminobenzoic Acid Ester of 4-(2-Hydroxyethoxy)-dibenzoylmethane | 5.00 | — |
| Dimethyl Isosorbide | 5.00 | — |
| Dioctyl Maleate | 8.00 | 5.00 |
| $C_{12}$–$C_{15}$ Alcohol Benzoate (Finsolv TN - commercially available from Finetex, Inc.) | 4.00 | 2.00 |
| Glycerin | 3.50 | 3.50 |
| Ethylene Acrylate Copolymer | 3.80 | 3.80 |
| 1-(2',3',4',5'-tetramethylphenyl)-1,3-butanedione | 2.00 | 2.00 |
| Cetyl Alcohol | 1.75 | 1.75 |
| Polyoxyethylene Stearyl Alcohol (commercially available in the Brij series from ICI Americas, Inc.) | 1.75 | 1.75 |
| Stearic Acid | 1.25 | 1.25 |
| Glyceryl Stearate | 1.13 | 1.13 |
| Alkyl Parabens | 0.90 | 0.90 |
| Titanium Dioxide | 0.40 | — |
| Dimethicone | 0.30 | 0.30 |
| Carbomer viscosity control agents (commercially available as Acritamer from R.I.T.A. Corp.) | 0.23 | 0.23 |
| Imidazolidinyl Urea | 0.10 | 0.10 |
| Potassium Hydroxide | 0.15 | 0.15 |
| Tyrosine | 0.10 | 0.10 |
| Tetrasodium EDTA | 0.10 | 0.10 |
| Water | qs | qs |

These lotions are useful for topical application to inhibit damage caused by radiation, particularly acute or chronic UV exposure. Use of an amount of lotion sufficient to deposit about 0.5 mg/cm² of 1-(2',3',4',5'-tetramethylphenyl)-1,3-butanedione to the skin prior to radiation exposure is appropriate.

EXAMPLES 6 & 7

Suntan creams are prepared by combining the following components utilizing conventional mixing techniques.

| Component | Percent by Weight of Composition | |
| --- | --- | --- |
| | Example 6 | Example 7 |
| Mineral Oil | 20.00 | 20.00 |
| Octyl Palmitate | 10.00 | 10.00 |
| Glyceryl Isostearate | 4.00 | 4.00 |
| Octyl Methoxycinnamate | 7.50 | — |
| Oxybenzone | 3.00 | — |
| Polyethylene (AC-617-A, AC-6-A available from Allied Chemical) | 2.00 | 2.00 |
| Alkyl parabens | 0.30 | 0.30 |
| Glycerin | 2.00 | 2.00 |
| 1-(2',3',4',5'-tetramethylphenyl)-1,3-butanedione | 2.00 | 5.00 |
| Ibuprofen | 1.00 | — |
| Water | q.s. | q.s. |

These creams are useful for topical application to inhibit damage caused by radiation, particularly acute or chronic UV exposure. Use of an amount of cream sufficient to deposit about 0.5 mg/cm² and 1.2 mg/cm² of 1-(2',3',4',5'-tetramethylphenyl)-1,3-butanedione to the skin for Examples 6 and 7, respectively, is appropriate.

EXAMPLE 8

A suntan stick is prepared by combining the following components utilizing conventional mixing techniques.

| Component | Percent by Weight of Composition |
|---|---|
| Candelilla Wax | 20.00 |
| Ozokerite Wax | 20.00 |
| Petrolatum | 20.00 |
| Lanolin | 15.00 |
| Mineral Oil | 14.85 |
| Octyl Dimethyl PABA | 4.00 |
| Benzophenone-3 | 1.00 |
| BHA (preservative: butylated hydroxy anisole) | 0.05 |
| Propylparaben | 0.10 |
| 1-(2',3',4'-trimethylphenyl)-1,3-butanedione | 5.00 |

This stick is useful for topical application, for example to the lips, to inhibit damage caused by radiation, particularly acute or chronic UV exposure. Use of an amount of stick sufficient to deposit about 1.0 mg/cm$^2$ of 1-(2',3',4'-trimethylphenyl)-1,3-butanedione to the lips prior to UV exposure is appropriate.

EXAMPLE 9

A suntan cream is prepared by combining the following components utilizing conventional mixing techniques.

| Component | Percent by Weight of Composition |
|---|---|
| Tetrasodium EDTA | 0.05 |
| Alkylparabens | 0.30 |
| Carbopol (polyacrylic acid polymer-commercially available from B. F. Goodrich Chemical) | 0.20 |
| Glycerin | 2.00 |
| Laureth-23 (polyethylene glycol ether of lauryl alcohol) | 3.00 |
| Sorbitan Stearate | 1.50 |
| Octyl Dimethyl PABA | 3.00 |
| Dimethicone | 2.00 |
| Stearyl Alcohol | 6.00 |
| Triethanolamine | 0.20 |
| 1-(2',4'-dimethylphenyl)-1,3-butanedione | 1.00 |
| Water | q.s. |

This cream is useful for topical application to inhibit damage caused by radiation, particularly acute or chronic UV exposure. Use of an amount of cream sufficient to deposit about 0.2 mg/cm$^2$ of 1-(2',4'-dimethylphenyl)-1,3-butanedione to the skin prior to UV exposure is appropriate.

EXAMPLE 10

A suntan aqueous face gel is prepared by combining the following components utilizing conventional-mixing techniques.

| Component | Percent by Weight Of Composition |
|---|---|
| Water | 50.00 |
| Aloe | 38.00 |
| Carbopol | 1.00 |
| Glycerin | 3.00 |
| Methylparaben | 0.20 |
| Triethanolamine | 0.90 |
| 2-Phenylbenzimidazole-5-sulfonic acid | 2.00 |
| Octoxynol-13 (ethoxylated alkyl phenol $(C_8H_{17})(C_6H_4)(OCH_2CH_2)_nOH$, n = av. val. 13) | 1.50 |
| 1-(2',3',4',5'-tetramethylphenyl)-1,3-butanedione | 2.00 |

| Component | Percent by Weight Of Composition |
|---|---|
| Color and Fragrance | q.s. |

This aqueous gel is useful for application to the face to inhibit damage caused by radiation, particularly acute or chronic UV exposure. Use of an amount of gel to deposit about 0.5 mg/cm$^2$ of 1-(2',3',4',5'-tetramethylphenyl)-1,3-butanedione to the face prior to UV exposure is appropriate.

EXAMPLE 11

A suntan gel is prepared by combining the following components utilizing conventional mixing techniques.

| Component | Percent by Weight of Composition |
|---|---|
| Ozokerite Wax | 10.00 |
| Paraffin | 10.00 |
| Petrolatum | 10.00 |
| Isopropyl Myristate | 5.00 |
| Mineral Oil | 58.00 |
| Octyl Methoxycinnamate | 2.50 |
| Propylparaben | 0.10 |
| BHA | 0.05 |
| 1-(2',3',4'-triethylphenyl)-1,3-butanedione | 2.00 |
| Naproxen | 2.00 |
| Fragrance and Color | q.s. |

This suntan gel is useful for topical application to inhibit damage caused by radiation, particularly acute or chronic UV exposure. Use of an amount of gel to deposit about 0.5 mg/cm$^2$ of 1-(2',3',4'-triethylphenyl)-1,3-butanedione to the skin is appropriate.

EXAMPLE 12

A suntan oil is prepared by combining the following components utilizing conventional mixing techniques.

| Component | Percent by Weight Of Composition |
|---|---|
| Sesame Oil | 5.0 |
| Cyclomethicone | 20.0 |
| Isopropyl Myristate | 5.0 |
| BHA | 0.05 |
| Sorbitan Oleate | 1.0 |
| Octyl Methoxycinnamate | 1.5 |
| Propylparaben | 0.7 |
| 1-(2',5'-diethylphenyl)-1,3-butanedione | 3.00 |
| Mineral Oil | q.s. |

This suntan oil is useful for topical application to inhibit damage caused by radiation, particularly acute or chronic UV exposure. Use of an amount of oil sufficient to deposit about 0.8 mg/cm$^2$ of 1-(2',5'-diethylphenyl-1,3-butanedione to the skin prior to UV exposure is appropriate.

EXAMPLE 13

A moisturizing oil-in-water-in-silicone sunscreen emulsion lotion is formed from the following ingredients.

| Ingredient | Percent by Weight of Composition |
|---|---|
| Aqueous Phase: | |

-continued

| Ingredient | Percent by Weight of Composition |
| --- | --- |
| Water | 58.32 |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodium alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |
| Color & Fragrance: | |
| FD&C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic $C_{11}$-$C_{15}$ fatty alcohol, av. 3 moles EO) | 2.00 |
| Octyl Methoxycinnamate | 7.00 |
| Benzophenone-3 | 0.50 |
| Naproxen | 2.00 |
| 1-(2',3',4',5'-tetramethylphenyl)-1,3-butanedione | 2.00 |
| $C_{12}$-$C_{15}$ Alcohols Benzoate | 2.85 |

In a suitably sized vessel equipped with a suitable mechanical stirrer (Tekmar Model RW-20 stirring motor, manufactured by IKA-WERK, Germany), the water, pantethine, methylparaben, glycerine and sulfonate emulsifier are heated to about 72°–75° C. and mixed. Stirring is increased until a vortex forms in the aqueous solution. The thickener, Carbomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen, and 1-(2',3',4',5'-tetramethylphenyl)-1,3-butanedione are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°–50° C. and the colorant and odorant oil are added followed by cooling to room temperature (about 25° C.) with continued moderate agitation.

The four silicone fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturizing lotion is useful for topical application to inhibit damage caused by radiation, particularly acute or chronic UV exposure. Use of an amount of lotion sufficient to deposit about 0.5 mg/cm$^2$ of 1-(2',3',4',5'-tetramethylphenyl)-1,3-butanedione to the skin is appropriate. This lotion may also be applied several times daily, e.g., 2 or 3 times daily, for extended periods of time, i.e., greater than one week, in amounts sufficient to deposit about 0.5 mg/cm$^2$ of 1-(2',3',4',5'-tetramethylphenyl)-1,3-butanedione to the skin to inhibit damage caused by chronic UV exposure.

EXAMPLE 14

A skin conditioning toilet bar is prepared from the following ingredients.

| Component | Percent by Weight of Composition |
| --- | --- |
| Tallow/Coconut Soap (50/50) | 61.61 |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| 1-(2',3',4'-trimethylphenyl)-1,3-butanedione | 5.00 |
| Perfume | 1.40 |
| NaCl | 1.04 |
| Na$_2$SO$_4$ | 0.34 |
| Na$_4$EDTA | 0.06 |
| TiO$_2$ | 0.20 |
| Jaguar C15 (guar hydroxypropyltrimonium chloride) | 1.00 |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°–200° F. (65°–94° C.). About 10.0 parts of the hydrated polymer JAGUAR C-15 are mixed in. The 1-(2',3',4'-trimethylphenyl)-1,3-butanedione is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part TiO$_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°–105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

The use of this toilet bar for cleansing provides a useful means for deposition of 1-(2',3',4'-trimethylphenyl)-1,3-butanedione to the skin to inhibit damage caused by radiation, particularly acute or chronic UV exposure. Use of the toilet bar such that about 0.05 mg/cm$^2$ of 1-(2',3',4'-trimethylphenyl)-1,3-butanedione is deposited on the skin is appropriate.

EXAMPLE 15

Facial Cleanser

A facial cleanser (lathering mousse composition) is prepared from the following ingredients.

| Emulsion Concentrate (A) | Percent by Weight of Composition |
| --- | --- |
| DRO Water[1] | 52.63 |
| 2-Hydroxypropyglyceryl Ether | 15.00 |
| Sodium Glyceryl Ether Sulfonate (90% Coconut/10 Tallow) - 50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| 1-(2',3',4',5'-tetraethylphenyl)-1,3-butanedione | 5.00 |
| Jaguar C14-S (guar hydroxypropyl-trimonium chloride) | 0.25 |
| Perfume | 0.20 |
| FD&C Red Dye #4 | 0.20 |
| Lauryl Alcohol | 0.20 |
| Alkyl Parabens | 0.30 |
| Germall 115 (Imidazolidinyl urea) | 0.10 |
| Na$_4$EDTA | 0.10 |

[1]Water purified by double reverse osmosis

A-46 Propellant (Isobutane-Propane) (B)

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and 1-(2',3',4',5'-tetraethylphenyl)-1,3-butanedione. The mixture is then cooled to 135°–140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of 1-(2',3',4',5'-tetraethylphenyl)-1,3-butanedione to the skin to inhibit damage caused by radiation, particularly acute or chronic UV exposure. Use of amount of facial cleanser sufficient to deposit about 0.05 mg/cm$^2$ of 1-(2',3',4',5'-tetraethylphenyl)-1,3-butanedione to the skin is appropriate.

EXAMPLE 16

A cream Soap is prepared by combining the following ingredients as described below.

| Component | Percent by Weight of Composition |
| --- | --- |
| Sodium Lauroyl Glutamate (Acylglutamate LS-11) (28) | 22.00 |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| 1-(2',3',4'-tributylphenyl)-1,3-butanedione | 3.00 |
| Tocopherol Sorbate | 5.00 |
| Flufenamic Acid | 2.00 |
| 2-Ethylhexyl Methoxycinnamate | 3.00 |
| Water | 30.50 |
| Glycerin | 10.00 |
| Fragrance and Preservative | q.s. |

The sodium glutamate, sodium hydrogenated tallow glutamate and cocoyl glutamate, polyethylene glycol, polyethylene glycol monostearate, polyoxyethylene sorbitan monostearate, 1-(2',3',4',5'-tributylphenyl)-1,3-butanedione, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of 1-(2',3',4'-tributylphenyl)-1,3-butanedione to the skin to inhibit damage caused by radiation, particularly acute or chronic UV exposure. Use of an amount of cream soap sufficient to deposit about 0.05 mg/cm$^2$ of 1-(2',3',4'-tributylphenyl)-1,3-butanedione to the skin is appropriate.

EXAMPLE 17

A shampoo composition is made by combining the following components.

| Component | Percent by Weight of Composition |
| --- | --- |
| Ammonium Lauryl Sulfate | 12.0 |
| Ammonium Xylene Sulfonate | 2.2 |
| Ammonium Laureth Sulfate | 4.0 |
| NaCl | 0.5 |
| 1-(2',5'-dimethylphenyl)-1,3-butanedione | 5.0 |
| Octyl Dimethyl PABA | 7.0 |
| Water | 68.1 |
| Perfume and Minor Ingredients | 1.2 |

The ammonium lauryl sulfate, ammonium laureth sulfate, and ammonium xylene sulfonate are first mixed together. The 1-(2',5'-dimethylphenyl)-1,3-butanedione and octyl dimethyl PABA and perfume and minor ingredients are added and the resulting mixture is agitated in a Teckmare Mill set at 70 for 2 minutes at 70° C.

The resulting shampoo composition is added to hair which has been wetted with water, worked through the hair then rinsed out. This allows for deposition of 1-(2',5'-dimethylphenyl)-1,3-butanedione and octyl dimethyl PABA to the scalp to inhibit damage caused by acute or chronic UV exposure. Use of an amount of shampoo sufficient to deposit about 0.05 mg/cm$^2$ of 1-(2',5'-dimethylphenyl)-1,3-butanedione to the scalp is appropriate.

EXAMPLES 18 & 19

Simple solutions are made by combining the following components:

| Component | Percent by Weight of Composition | |
| --- | --- | --- |
| | Example 18 | Example 19 |
| Propylene glycol | 27.6 | 28.5 |
| Ethanol, absolute | 46.1 | 47.5 |
| Water | 21.3 | 22.0 |
| 1-(2',3',4',5'-tetramethylphenyl)-1,3-butanedione | 5.0 | 2.0 |

The propylene glycol, ethanol and water are first mixed together in proportions of 25:55:20 v:v:v, respectively. This solution is then combined with 1-(2',3',4',5'-tetramethylphenyl)-1,3-butanedione in proportions of 95:5 w:w for Example 18 and 98:2 w:w for Example 19 to produce the final solutions. Topical application of these solutions in an amount sufficient to deposit about 0.2 mg/cm$^2$ for Example 18 and 0.07 mg/cm$^2$ for Example 19 of 1-(2',3',4',5'-tetramethylphenyl)-1,3-butanedione to the skin inhibits damage caused by radiation, particularly acute or chronic UV exposure.

While particular embodiments of the subject invention have been described, it will be obvious to those skilled in the art that various changes and modifications of the subject invention can be made without departing from the spirit and the scope of the invention. It is intended to cover, in the appended claims, all such modifications that are within the scope of this invention.

What is claimed is:

1. A photoprotective composition comprising:
   A. A safe and effective amount of a compound having the structure:

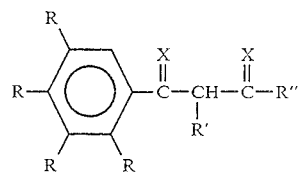

wherein each R is independently $C_1$–$C_{20}$ alkyl or hydrogen, at least two being alkyl; R' is hydrogen, or $C_1$–$C_{20}$ alkyl or aryl; R" is $C_1$–$C_{20}$ alkyl or halo; and each X is independently oxygen or sulfur; and
   B. a cosmetically-acceptable topical carrier.

2. The composition of claim 1 wherein R" is alkyl.

3. The composition of claim 1 wherein R' is hydrogen.

4. The composition of claim 2 wherein each alkyl R is $C_1$–$C_4$, R' is hydrogen or $C_1$–$C_8$ alkyl, and R" is $C_1$–$C_8$ alkyl.

5. The composition of claim 4 wherein each alkyl R, R' and R" is unsubstituted and saturated.

6. The composition of claim 5 wherein R' is hydrogen.

7. The composition of claim 6 wherein each X is oxygen.

8. The composition of claim 7 wherein R" is $C_1$–$C_4$, and each alkyl R is methyl or ethyl.

9. The composition of claim 8 wherein each alkyl R is methyl and R" is methyl.

10. The composition of any of claims 1, 5, 8 or 9 wherein at least 3 of the R's are alkyl.

11. The composition of claim 9 wherein all four R's and R" are methyl.

12. The composition of claim 9 wherein the three R's in the 2'-, 3'- and 4'-positions are methyl, the R in the 5'-position is hydrogen, and R" is methyl.

13. The composition of any of claims 1, 5, 8, 9, 11 and 12 wherein the composition comprises from about 0.5% to about 10% of the compound and from about 5% to about 20% of an emollient.

14. The composition of any of claims 1, 7 and 9 wherein the composition also comprises an active agent selected from the group consisting of a sunscreen, a sunblock, an anti-inflammatory, an antioxidant and a radical scavenger.

15. The composition of any of claims 1, 7 and 9 wherein the composition comprises an additional sunscreen compound.

16. A method for protecting the skin of a human or lower animal from radiation by topically administering to the skin a safe and effective amount of the composition of any of claims 1, 7 and 9.

17. A method for protecting the skin of a human or lower animal from radiation by topically administering to the skin a safe and effective amount of the composition of any of claims 1, 5, 8, 9, 11 and 12 at least about once daily for more than 6 months.

* * * * *

UNITED STATES PATENT AND TRADEMARK OFFICE
CERTIFICATE OF CORRECTION

PATENT NO. : 5,439,954
DATED : August 8, 1995
INVENTOR(S) : Rodney D. Bush

It is certified that error appears in the above-indentified patent and that said Letters Patent is hereby corrected as shown below:

Column 6, line 21, "2°'" should read --2'--.
Column 9, line 57, "Segatin" should read --Segarin--.
Column 9, line 64, "Dickeft" should read --Dickert--.
Column 20, line32, "lenamates" should read --fenamates--.
Column 22, line 52, "Stll i l l" should read --still--.
Column 23, line 66, "5.00" should read --2.00--.

Signed and Sealed this

Twelfth Day of November, 1996

Attest:

BRUCE LEHMAN

*Attesting Officer*  *Commissioner of Patents and Trademarks*